(12) United States Patent
Oakes et al.

(10) Patent No.: US 12,254,969 B2
(45) Date of Patent: Mar. 18, 2025

(54) VERIFICATION BYPASS IN A DISPENSING PHARMACY

(71) Applicant: McKesson Corporation, Irving, TX (US)

(72) Inventors: Juston Oakes, San Angelo, TX (US); Hommy Lopez, Plainfield, IL (US)

(73) Assignee: McKesson Corporation, Irving, TX (US)

( * ) Notice: Subject to any disclaimer, the term of this patent is extended or adjusted under 35 U.S.C. 154(b) by 595 days.

(21) Appl. No.: 17/566,816

(22) Filed: Dec. 31, 2021

(65) Prior Publication Data

US 2023/0215536 A1 Jul. 6, 2023

(51) Int. Cl.
*G16H 20/13* (2018.01)
*G07F 17/00* (2006.01)
*G16H 40/67* (2018.01)
*G16H 70/40* (2018.01)

(52) U.S. Cl.
CPC ......... *G16H 20/13* (2018.01); *G07F 17/0092* (2013.01); *G16H 40/67* (2018.01); *G16H 70/40* (2018.01)

(58) Field of Classification Search
CPC .......................... G07F 17/0092; G06H 20/13
See application file for complete search history.

(56) References Cited

U.S. PATENT DOCUMENTS

| 2006/0041330 A1* | 2/2006 | Ansari | G06Q 10/087 |
| | | | 700/240 |
| 2015/0066205 A1* | 3/2015 | Braun | G16H 20/13 |
| | | | 700/235 |

* cited by examiner

*Primary Examiner* — Timothy R Waggoner
(74) *Attorney, Agent, or Firm* — Ballard Spahr LLP

(57) ABSTRACT

Technologies are provided for verification bypass in an automated dispensing pharmacy. In some embodiments, a computing system can identify a first automation device from a group of automation devices that dispense unit-of-use packages. The computing system can then cause a state of verification bypass for the first automation device to transition to an active state at a first time. At a second time after the first time, the computing system can detect dispense of a unit-of-use package from the first automation device, and can then determine that a time interval elapsed from the first time to the second time is less than or equal to a defined duration. The computing system can therefore designate the unit-of-use package as a verified item.

20 Claims, 7 Drawing Sheets

VERIFICATION BYPASS IN A DISPENSING PHARMACY

SUMMARY

It is to be understood that both the following general description and the following detailed description are illustrative and explanatory only and are not restrictive.

In one embodiment, the disclosure provides a computing system. The computing system includes at least one processor; and at least one memory device having processor-executable instructions stored thereon that, in response to execution by the at least one processor, cause the computing system to identify a first automation device from a group of automation devices that dispense unit-of-use packages, and cause a state of a verification bypass for the first automation device to transition to an active state at a first time. The processor-executable instructions, in response to execution by the at least one processor, also cause the computing system to detect, at a second time after the first time, dispense of a unit-of-use package from the first automation device. The processor-executable instructions, in response to execution by the at least one processor, further cause the computing system to determine that a time interval elapsed from the first time to the second time is less than or equal to a defined duration, and designate the unit-of-use package as a verified item in response to detecting the dispense of the unit-of-use package.

In another embodiment, the disclosure provides a computer-implemented method. The computer-implemented method includes identifying, by a dispensing pharmacy system, a first automation device from a group of automation devices that dispense unit-of-use packages, and causing, by the dispensing pharmacy system, a state of a verification bypass for the first automation device to transition to an active state at a first time. The computer-implemented method also includes detecting, by the dispensing pharmacy system, at a second time after the first time, dispense of a unit-of-use package from the first automation device. The computer-implemented method further includes determining, by the dispensing pharmacy system, that a time interval elapsed from the first time to the second time is less than or equal to a defined duration, and designating, by the dispensing pharmacy system, the unit-of-use package as a verified item in response to detecting the dispense of the unit-of-use package.

In yet another embodiment, the disclosure provides a computer-program product. The computer-program product includes at least one computer-readable non-transitory storage medium having processor-executable instructions stored thereon that, in response to execution, cause a computing system to identify a first automation device from a group of automation devices that dispense unit-of-use packages, and cause a state of a verification bypass for the first automation device to transition to an active state at a first time. The processor-executable instructions, in response to execution, also cause the computing system to detect, at a second time after the first time, dispense of a unit-of-use package from the first automation device. The processor-executable instructions, in response to execution, further cause the computing system to determine that a time interval elapsed from the first time to the second time is less than or equal to a defined duration, and designate the unit-of-use package as a verified item in response to detecting the dispense of the unit-of-use package.

Additional elements or advantages of this disclosure will be set forth in part in the description which follows, and in part will be apparent from the description, or may be learned by practice of the subject disclosure. The advantages of the subject disclosure can be attained by means of the elements and combinations particularly pointed out in the appended claims.

This summary is not intended to identify critical or essential features of the disclosure, but merely to summarize certain features and variations thereof. Other details and features will be described in the sections that follow. Further, both the foregoing general description and the following detailed description are illustrative and explanatory only and are not restrictive of the embodiments of this disclosure.

BRIEF DESCRIPTION OF THE DRAWINGS

The annexed drawings are an integral part of the disclosure and are incorporated into the subject specification. The drawings illustrate example embodiments of the disclosure and, in conjunction with the description and claims, serve to explain at least in part various principles, elements, or aspects of the disclosure. Embodiments of the disclosure are described more fully below with reference to the annexed drawings. However, various elements of the disclosure can be implemented in many different forms and should not be construed as limited to the implementations set forth herein. Like numbers refer to like elements throughout.

DETAILED DESCRIPTION

Figure 1:
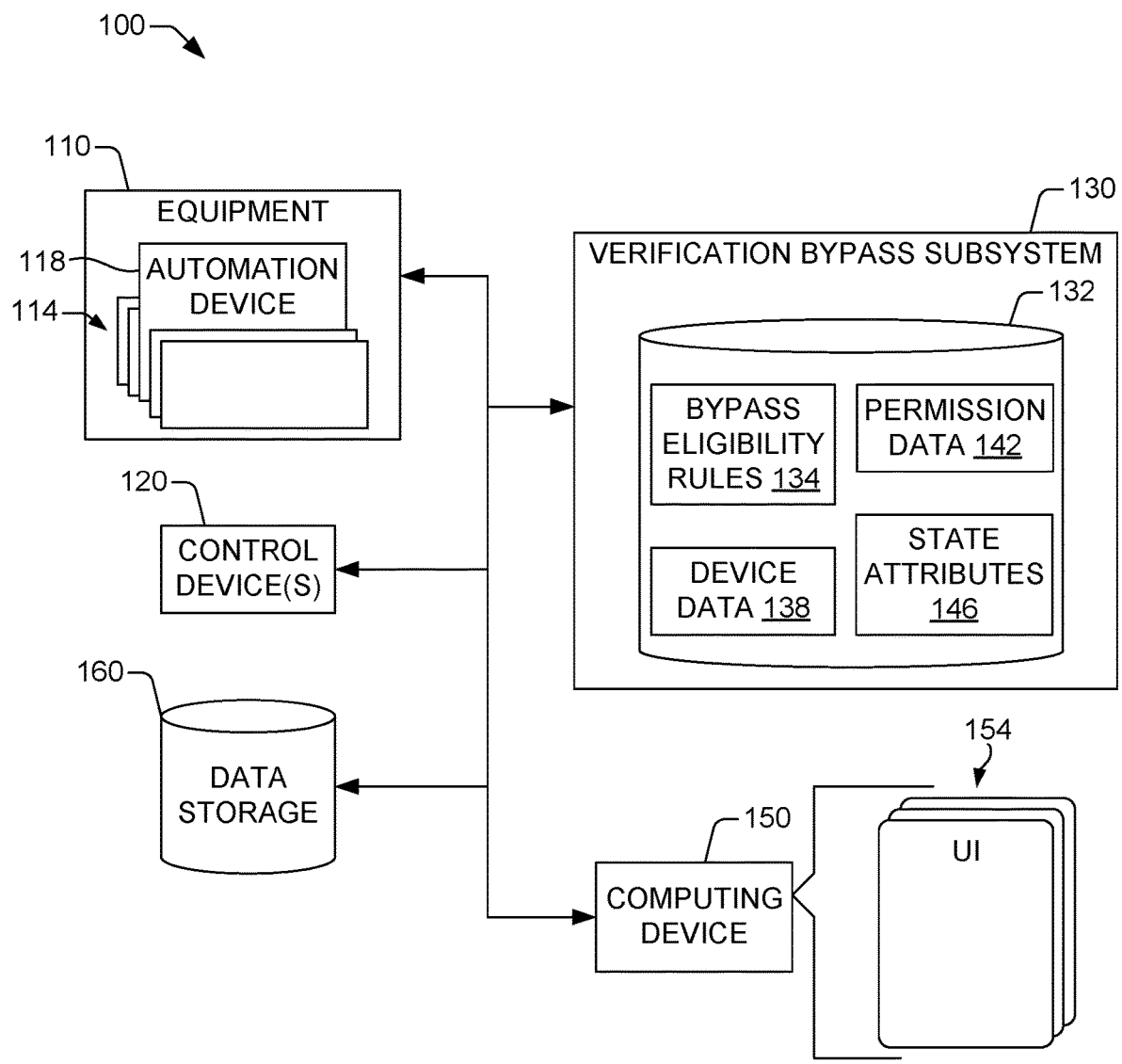
FIG. 1 illustrates an example of an operating environment for verification bypass in a dispending pharmacy, in accordance with one or more embodiments of this disclosure.

The disclosure recognizes and addresses, among other technical challenges, the issue of configuration of bypass of a verification stage during fulfillment of a prescription in an automated dispensing pharmacy. Such a bypass can be referred to as verification bypass. While existing automation processes can permit bypassing such a verification stage in bulk dispensing of tablets and capsules, commonplace automated dispensing pharmacies are unable to bypass the verification of products dispensed in units-of-use packages. In this disclosure, a unit-of-use package refers to an original container for a legend medication, sealed and labeled, prelabeled by the manufacturer. The container has sufficient medication for one normal course of therapy. The inability to bypass the verification of units-of-use package can hinder the operational efficiency of an automated dispensing pharmacy, thus limiting throughput due to individual verification of every prescription involving a unit-of-use package.

Embodiments of this disclosure provide computing systems, computer-implemented methods, and computer program products that, individually or in combination, provide verification bypass of unit-of-use packages in an automated dispensing pharmacy. To that end, embodiments of the disclosure can identify a first automation device from a group of automation devices that dispense unit-of-use packages, and can then cause a state of verification bypass for the first automation device to transition to an active state at a first time. At a second time after the first time, embodiments of this disclosure can detect dispense of a unit-of-use package from the first automation device, and can then determine if a time interval elapsed from the first time to the second time is less than or equal to a defined duration. In response to determining that the time interval does not exceed the defined duration, embodiments of this disclosure can designate the unit-of-use package as a verified item.

Because embodiments of this disclosure avoid human intervention in the verification of unit-of-use packages, errors associated with such verification can be mitigated, if not avoided altogether. Besides mitigating human errors, verification bypass as is described herein also can reduce the amount of human resources that might be involved various aspects of fulfilling a prescription. As an illustration, implementing verification bypass during the fulfillment of about 300 prescriptions can reduce the involvement of a human agent (e.g., a pharmacist) by approximately one hour. Additionally, embodiments of this disclosure simplify automation processes to fulfill prescriptions involving unit-of-use packages. As a result, embodiments of this disclosure improve the operational efficiency of an automated dispensing pharmacy relative to existing technologies. Further, embodiments of this disclosure also can permit reducing the footprint of an automated dispensing pharmacy, with the ensuing improved use space and improved consumption of energy.

With reference to the drawings, FIG. 1 schematically illustrates an example of an operating environment 100 for verification bypass in a dispending pharmacy, in accordance with one or more embodiments of this disclosure. The operating environment 100 constitutes a dispensing pharmacy, such as a mail order pharmacy or a hub of a central-fill platform. The dispensing pharmacy has the licensure to dispense medications, and also has an NPI number and an NCPDP processor identification number (or BIN). The dispensing pharmacy can include multiple devices that can perform automation processes to fulfill prescription fill requests and ship a package containing one or multiple medications to a destination address (e.g., a dwelling of a subject, a nursing home, an assisted-living facility, or similar). Thus, the dispensing pharmacy in accordance with this disclosure can be referred to as an automated dispensing pharmacy.

As such, the operating environment 100 includes automation equipment 110 and one or multiple control devices 120. The automation equipment 110 can include dispensing hoppers, conveyance systems, camera devices, weight scales, radio-frequency identification (RFID) reader devices, printing devices, and similar equipment. More specifically, in some embodiments, the equipment 110 can include a group of automation devices 114, where each automation device in that the group dispenses unit-of-use packages. In some cases, a first automation device of the group of automation devices 114 can dispense unit-of-use packages for a first prescription medication, and a second automation device can dispense unit-of-use packages for a second prescription medication. In other cases, the first automation device and the second automation device can dispense unit-of-use packages for a same prescription medication. Simply for purposes of illustration, unit-of-use packages can include blister packs, metered-dose inhalers, course-of-therapy vials, and the like. The control device(s) 120 can control the operation of at least some of the equipment 110 in order to execute an automation process to fulfill a prescription fill request. A bus architecture (represented by connected arrows) permit exchanging data and/or signaling among the equipment 110 and the control device(s) 224.

The operating environment 100 also includes a verification bypass subsystem 130 that can identify one or more automation devices of the group of automation devices 114 as being eligible for verification bypass. To that end, the verification bypass subsystem 130 can apply one or more rules to operating state data identifying an operating condition of an automation device of the group of automation devices 114. The rule(s), individually or in combination, can dictate a constraint on the operation condition in order for the automation device to be eligible for verification bypass. Thus, each one of the rule(s) can be referred to as a bypass eligibility rule.

In one example, an eligibility rule dictates that a minimum number of unit-of-use packages must be present within an automation device. In another example, another eligibility rule dictates that a medication dispensed by the automation device must be allowed to be dispensed with verification bypass. In other words, that eligibility rule dictates that an indicator defining bypass eligibility for a particular national drug code (NDC) corresponding to the medication must be configured to "enabled" (or similar value) in order for the automation device to be eligible for verification bypass. Simply for purposes of illustration, NDC is a unique, 3-segment numeric identifier assigned to a medication that is regulated. The first segment of the NDC identifies the labeler (the company that manufactures or distributes the drug). The second segment identifies the product (e.g., strength, dosage form, and formulation). The third segment identifies package size and package type for unit-of-use package. In yet another example, another eligibility rule can dictate that automated dispense of a medication must include the generation of an as-dispensed image for a unit-of-use package and recordation of that image in a storage repository. That is, an automation device included in a dispense assembly that excludes acquisition and recordation of such an image is ineligible for verification bypass. In still another example, another eligibility rule dictates that information in one or more identifier fields on the unit-of-use package must match measured information during automated dispense from the automation device. An identifier field can be, for example, a universal product code (UPC) field or a field on a prescription label (or RX label) adhered to the unit-of-use package.

Bypass eligibility rule(s) can be retained within one or multiple memory elements 134 (referred to as eligibility rules 134) in data storage 132. The eligibility rules 134 can contain multiple rules in some cases.

Figure 2:
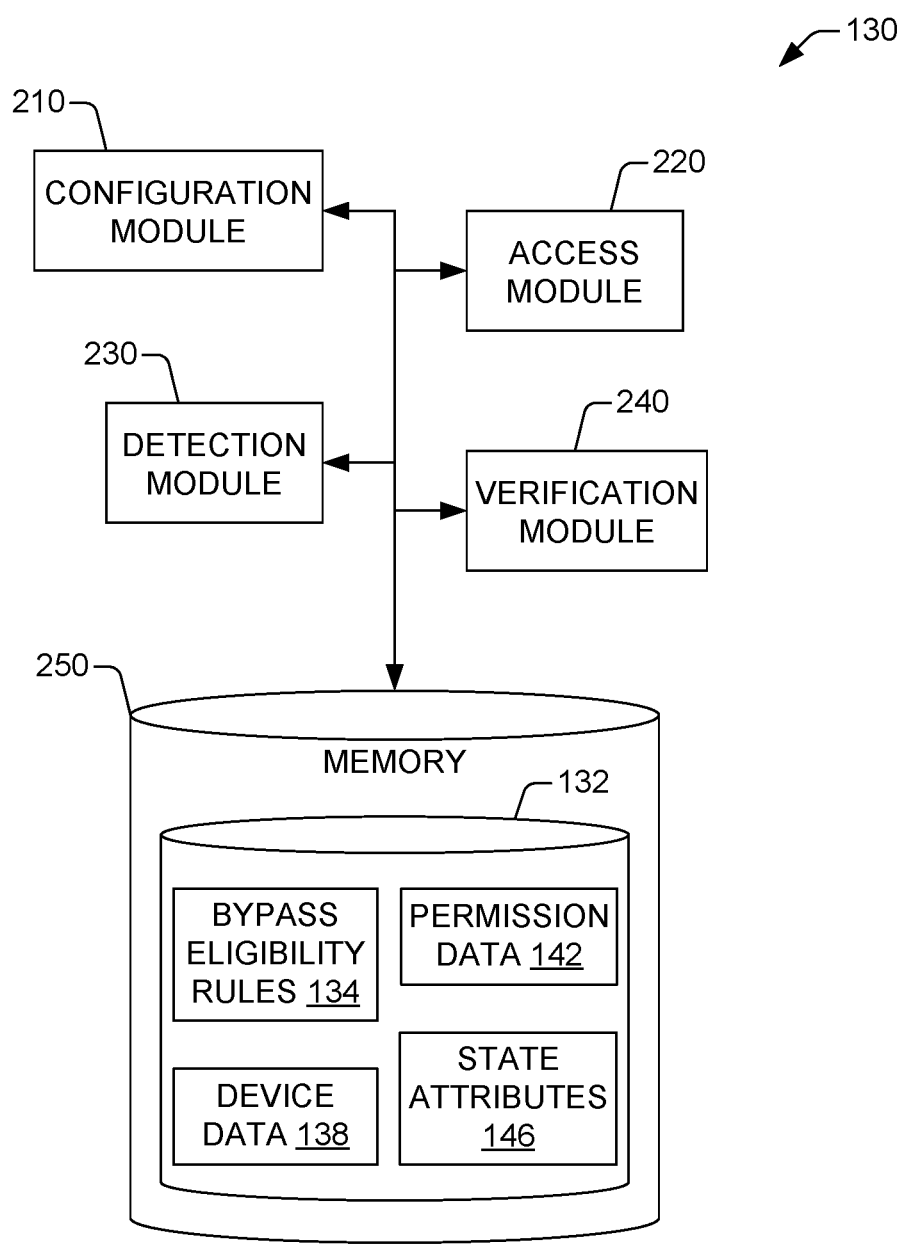
FIG. 2 illustrates an example of a computing system for verification bypass in a dispending pharmacy, in accordance with one or more embodiments of this disclosure.

In some instances, the verification bypass subsystem 130 can determine that the operating state data satisfies the rule(s). In response, the verification bypass subsystem 130 can determine that the automation device is eligible for verification bypass. Additionally, in further response, the verification bypass subsystem 130 can add data identifying the automation device to a data structure 138 (referred to as device data 138) identifying eligible automation devices within the group of automation devices 114. In some embodiments, as is illustrated in FIG. 2, the verification bypass subsystem 130 can include a configuration module 210 that can determine if an automation device is eligible for verification bypass by applying one or more eligibility rules to operating state data corresponding to the automation device. In response to the automation device being eligible, the configuration module 210 also can add data identifying the automation device to the device data 138. As is shown in FIG. 2, configuration module 210 can be functionally coupled to one or multiple memory devices 250 (referred to as memory 250) to output data to and retrieve data from the memory 250. The memory 250 can contain the data storage 132. A bus architecture (represented by arrows in FIG. 2) can permit the functional coupling between the configuration module 210 and the memory 250.

The operating environment 100 also includes a computing device 150 that can interact with the verification bypass subsystem 130 to configure verification bypass for one or several automation devices of the group of automation devices 114. Such an interaction can include the exchange of data that permits configuring the verification bypass. To interact with the verification bypass subsystem 130, the client device can present a sequence of user interfaces 154, where one or more user interfaces in that sequence can permit receiving input data defining attributes of the verification bypass. Those attributes can include, for example, identifiers that identify respective automation devices and/or durations of the verification bypass.

In some embodiments, as part of the sequence user interfaces 154, the computing device 150 can present a first user interface that permits accessing, under appropriate condition(s), the verification bypass subsystem 130. In one example, the first user interface can be embodied in a login interface having selectable indicia to access a software application (not depicted in FIG. 1) hosted by the verification bypass subsystem 130. An appropriate condition to access the software application can be valid user credentials for an agent account. In some cases, the agent account can include data identifying a pharmacist. The user credentials can include a username and a password, for example. The computing device 150 can receive input data indicative of the user credentials and, in some cases, can send the input data to the verification bypass subsystem 130.

The verification bypass subsystem 130 can receive the input data indicative of the user credentials and can determine if the user credentials can be authenticated. In response to authenticating the user credentials, the verification bypass subsystem 130 can grant access to the software application. The verification bypass subsystem 130 also can determine if the agent account has permission to activate verification bypass for one or more automation devices. To make such a determination, the verification bypass subsystem 130 can access permission data 142. The permission data 142 can include data indicative of a group of permissions corresponding to the agent account. In some instances, the group of permissions include permission to activate verification bypass for one or more eligible automation devices of the group of automation devices 114. In those instances, the data indicative of the group of permissions also can include data identifying the one or more eligible automation devices. Additionally, in those instances, the verification bypass subsystem 130 can determine that the agent account is permitted to activate verification bypass for such automation device(s). In some embodiments, as is illustrated in FIG. 2, the verification bypass subsystem 130 can include an access module 220 that can receive and authenticate credentials. The access module 220 also can determine if an agent account associated with the credentials has permission to activate verification bypass for an automation device. To accomplish such a determination, the access module 220 can use permission data 142 retained in the data storage 132 within the memory 250. As is shown in FIG. 2, the access module 220 can be functionally coupled to the memory 250 to output data to and retrieve data from the memory 250. The bus architecture (represented by arrows in FIG. 2) can permit the functional coupling between the access module 220 and the memory 250.

The verification bypass subsystem 130 also can cause the computing device 150 to present a first configuration user interface in response to the agent account being permitted to activate verification bypass. The first configuration user interface can be part of the sequence of user interfaces 154. The first configuration user interface can prompt selection of at least one of the eligible automation device(s). To that end, the first configuration user interface can include a selectable UI element having one or more markings prompting selection of an automation device. Selection of the selectable UI element causes the computing device 150 to present a second configuration user interface. The second configuration user interface can include selectable UI elements for respective ones of the eligible automation device(s). Selection of one of those selectable UI elements results in verification bypass being activated for a respective one of the eligible automation device(s). In some embodiments, the second configuration user interface can be embodied in a redrawn version of the first configuration user interface, where the redrawn version includes a visual element presented as an overlay. That visual element includes the selectable UI elements for respective ones of the eligible automation device(s). In some embodiments, configuration module 210 (FIG. 2) can cause presentation of such user interfaces.

Figure 3A:
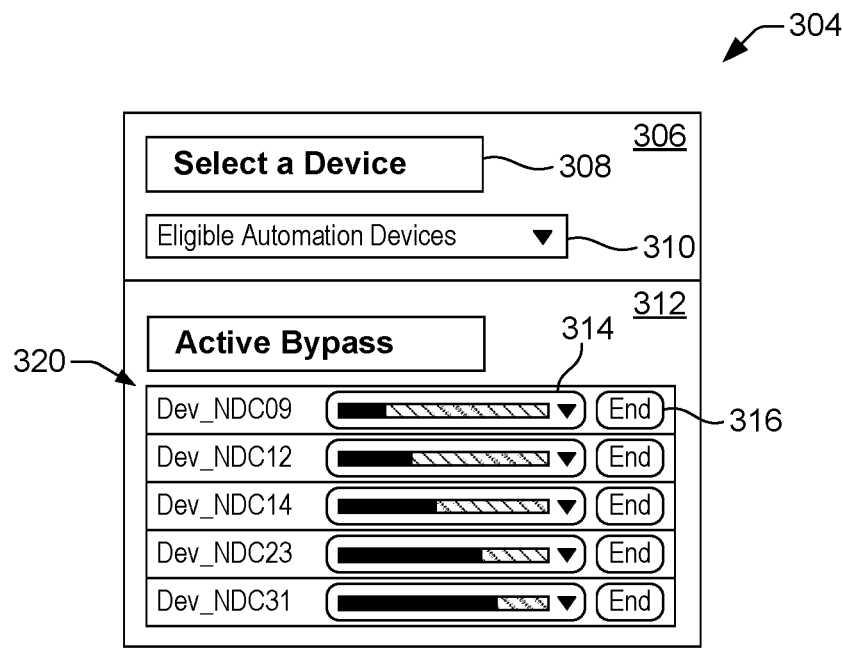
FIG. 3A illustrates an example of a user interface (UI) in accordance with one or more embodiments of this disclosure.

Simply for purposes of illustration, the UI 304 shown in FIG. 3A is an example of the first configuration user interface. The UI 304 includes a pane 306 having a UI element 308 that prompts selection of an automation device for verification bypass. The pane 306 also includes a selectable UI element 310. Selection of the selectable UI element 310 permits identifying a particular automation device for verification bypass. The UI 304 also includes a pane 312 presenting a list 320 of automation devices currently having an active verification bypass. Although the list 320 shown in the pane 312 in FIG. 3A includes several automation devices, fewer or more automation devices can be listed. Indeed, in some cases, the list may be empty because prior configuration of verification bypass may not have occurred.

Each item in that list is embodied in a respective visual element that includes text, or other markings, identifying an automation device; first selectable indicia 314; and second selectable indicia 316. The first selectable indicia 314 can include a first UI object and a second UI object (a triangle, simply as an example). The first UI object is depicted as a bar having a solid section and a hatched section, for the sake of illustration. The bar represents both a time that verification bypass has been active (solid section, for example) and a time remaining until verification bypass becomes inactive (hatched section, for example). Accordingly, the longitudinal length of the bar represents a current duration of verification bypass. The second UI object is a selectable indicium that can permit updating the current duration of verification bypass.

In turn, the second selectable indicia 316 can permit terminating the verification bypass for an automation device. Reactivation of verification bypass for such a device can be accomplished by subsequent selection of automation device for verification bypass. In some embodiments, additional selectable indicia can be presented besides the second selectable indicia 316. The additional selectable indicia can correspond to respective control elements. Selection of a first one of those control elements can cause verification bypass for the automation device to be paused. Selection of a second one of those control elements can cause the verification bypass for the automation device to be resumed. Regardless of how verification bypass is reactivated for the automation device, the configuration module 210 (FIG. 2), for example, can determine if an automation device is eligible for verification bypass prior to permitting reactivation of verification bypass.

Figure 3B:
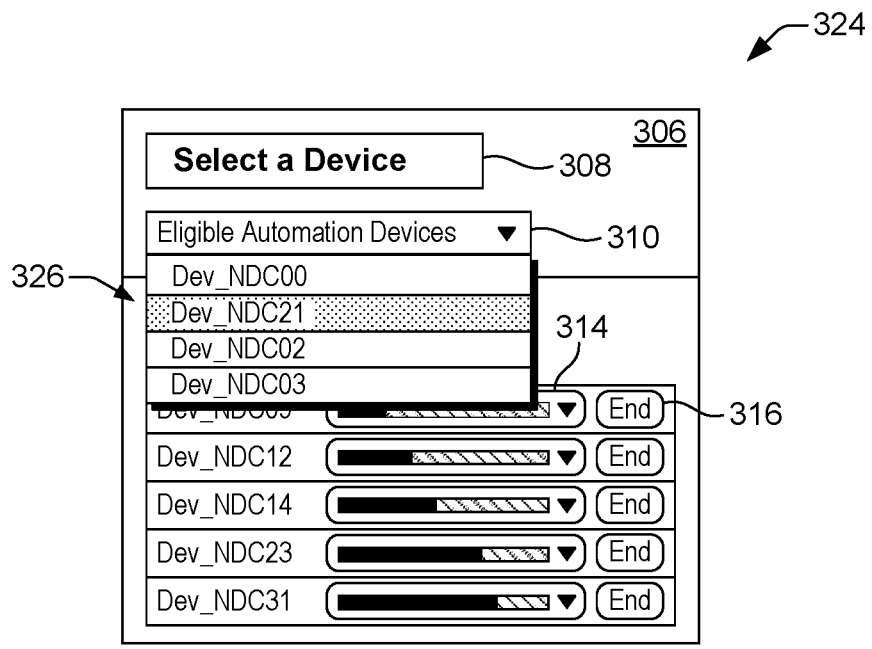
FIG. 3B illustrates an example of another UI in accordance with one or more embodiments of this disclosure.

In connection with identification of the particular automation device for verification bypass, in some embodiments, selection of the selectable UI element 310 causes the computing device 150 to present a configuration user interface 324 as is shown in FIG. 3B. The configuration user interface 324 is embodied in a redrawn version of the configuration user interface 304, where the redrawn version includes a visual element 326 presented as an overlay. The visual element 326 presents a menu of automation devices eligible for verification bypass. Each item in the menu is selectable and includes text, or other markings, identifying an eligible automation device. Selection of an item in the menu can cause the computing device 150 to redraw the visual element 326 with the item highlighted or otherwise marked (represented by a stippled block in FIG. 3B), to convey the selection of the eligible automated device for verification bypass.

With further reference to FIG. 1, selection of a particular selectable UI element can cause the computing device 150 to send data identifying a first automation device of the automation devices. The first automation device can be embodied in an automation device 118 in the group of automation devices 114. The data can be sent to the verification bypass subsystem 130. The verification bypass subsystem 130 can receive the data indicative of the particular automation device. In response, the verification bypass subsystem 130 can identify the first automation device for verification bypass. For instance, an alias identifying the first automation device can be "Dev_NDC21," and the data identifying that particular automation device can be the string of characters "Dev_NDC21." Embodiments of this disclosure are not limited to identifying an automation device in terms of an alias. The first automation device—and other automation devices of this disclosure—can be identified by serial number, MAC address, IP address, or similar. The configuration module 210 (FIG. 2) can identify the first automation device for verification bypass, in some embodiments.

The verification bypass subsystem 130 can then cause a state of verification bypass for the first automation device (e.g., the automation device 118) to transition to an active state at a first time (also referred to as activation time). In some embodiments, such a state can be represented by a state attribute (a scalar variable or a vector variable, for example) and causing that state to transition to the active state can include updating a value of the state attribute to a new value indicative of the verification bypass being active. The verification bypass subsystem 130 can retain the state attribute within one or multiple memory elements 146 (referred to as state attributes 146) in the data storage 132.

The configuration module 210 (FIG. 2) can cause a state of an automation device to transition to (and from, when appropriate) an active state.

Verification bypass for a selected automation device can have a defined duration. The defined duration is the lifespan of the active state of the verification bypass. In some cases, the defined duration can be equal to a preset time interval. In those cases, a state attribute (e.g., one of the state attributes 146) can be indicative of the preset time interval. The verification bypass subsystem 130 can associate that state attribute to a second state attribute representing the active state of verification bypass for the selected automation device. In that way, the state of the verification bypass for the selected automation device can identify both active state and defined duration of the active state.

In other cases, the defined duration can be configurable. To configure the defined duration, in some embodiments, the computing device 150 can present a selectable UI element within a user interface in the sequence of user interfaces 154. Such a selectable UI element can prompt configuration of the defined duration of the active state of the verification bypass. Selection of the selectable UI element can cause the computing device 150 to present a third configuration user interface that permits receiving input data indicative of the defined duration.

Figure 3C:
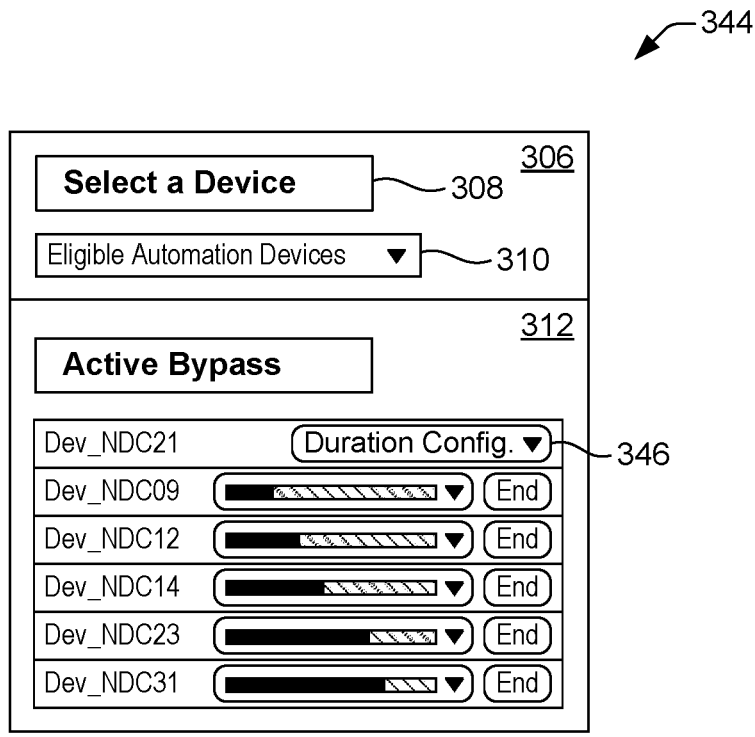
FIG. 3C illustrates an example of yet another UI in accordance with one or more embodiments of this disclosure.

For the sake of illustration, leveraging the example UIs shown in FIG. 3A and FIG. 3B, the UI 344 shown in FIG. 3C is an example of the user interface that includes a selectable UI element that prompts configuration of such a defined duration. The computing device 150 can present the UI 344 in response to the selection of the automation device labeled "DEV_NDC21" (FIG. 3B). Accordingly, the list shown in pane 312 in the UI 344 includes a visual element corresponding to such an automation device. The visual element includes text identifying the automation device; and selectable indicia 346 that prompts configuration of a duration of verification bypass for the automation device.

Figure 3D:
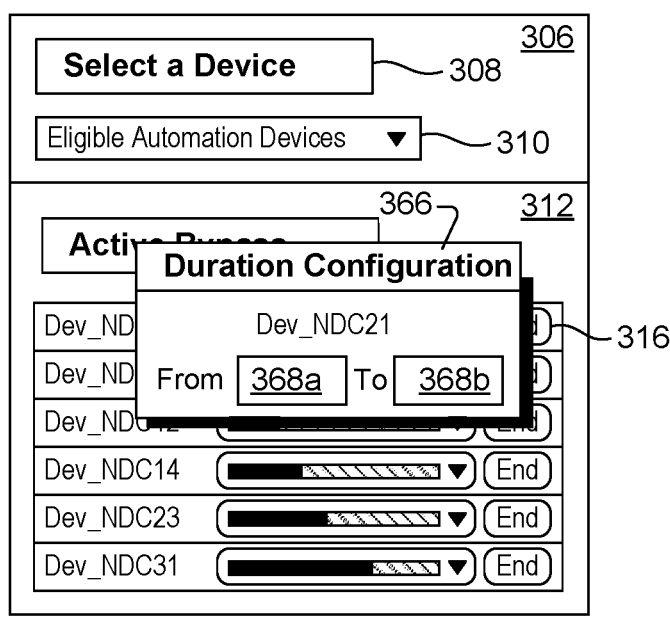
FIG. 3D illustrates an example of still another UI in accordance with one or more embodiments of this disclosure.

Selection of the selectable indicia 346 can cause presentation of the UI 364 shown in FIG. 3D. The UI 364 is an example of the third configuration user interface that permits receiving input data indicative of a defined duration. The UI 364 is embodied in a redrawn version of the UI 344 and includes a visual element 366 presented as an overlay. The visual element 366 permits defining the duration in terms of an initial instant and final instant. To that end, the visual element 366 includes a first selectable UI element 368*a* and a second selectable UI element 368*b* that can receive, respectively, first input data and second input data. The first input data defines the initial instant, and the second input data defines the final instant. Thus, a duration of verification bypass can be flexibly defined. For example, by defining the initial and final instants, the defined duration of verification bypass can be configured to be 1 hour and 33 minutes. As another example, the first input data can define the first instant as 8:00 AM, and the second input data can define the second instant as 10:00 AM. Accordingly, the defined duration of verification bypass can be configured to be two hours. Such a configuration may be beneficial if a pharmacist shift begins at 8:00 AM and a break is scheduled for 10:00 AM.

It is noted that the duration of the verification bypass is not limited to being defined in terms of initial and final instants. In some embodiments, the duration can be defined in terms of a single time interval (e.g., two hours, four hours, eight hours, or similar). To that end, in such embodiments, the UI 364 can present a single visual element that can receive input data defining the time interval. In one example, the time interval can be two hours, corresponding to a time period from beginning of a pharmacist shift to a break in that shift.

Regardless of how the input data indicative of the defined duration is obtained, the computing device 150 can send such input data to the verification bypass subsystem 130. Using that input data, the verification bypass subsystem 130 can update a state attribute (e.g., one of the state attributes 146) to be indicative of the preset time interval. The verification bypass subsystem 130 also can associate that state attribute to a second state attribute representing the active state of verification bypass for the selected automation device. Hence, the state of the verification bypass for the selected automation device can identify both active state and defined duration of the active state.

As noted, the first automation device selected for verification bypass can be part of the group of automation devices 114. Thus, the first automation device can dispense unit-of-use packages for a particular medication. Simply as an example, the first automaton device can dispense metered-dose inhalers. The verification bypass subsystem 130 can monitor dispense of unit-of-use packages from the first automation device. Thus, in some instances, the verification bypass subsystem 130 can detect dispense of a unit-of-use package from the first automation device. Dispense of the unit-of-use package can be detected at a second time after the first time (or activation time). In some embodiments, as is illustrated in FIG. 2, the verification bypass subsystem 130 can include a detection module 230 that can detect dispense of a unit-of-use package. To that end, the detection module 230 can monitor signaling from a control device that controls operation of the first automation device. In some cases, the detection module 230 can monitor such signaling by querying the control device in nearly real-time, periodically, or according to a schedule. In other cases, the detection module 230 can subscribe to a service provided by the control device, where the service supplies the signaling in response to a unit-of-use package being dispensed. In one example, the control device can be embodied in one of the control device(s) 120 and the first automation device can be embodied in the automation device 118. As is shown in FIG. 2, the detection module 230 can be functionally coupled to the memory 250 to output data to and retrieve data from the memory 250. The bus architecture (represented by arrows in FIG. 2) can permit the functional coupling between the detection module 230 and the memory 250.

Because verification bypass can be active for a defined duration, the verification bypass subsystem 130 can determine if a time interval elapsed from the first time to the second time exceeds the defined duration. That is, the verification bypass subsystem 130 can determine if that time interval is less than or equal to the defined duration.

In some cases, the verification bypass subsystem 130 can determine that the time interval exceeds the defined duration. In response, the verification bypass subsystem 130 can perform one or multiple exception operations. An exception operation can include, for example, causing the computing device 150 to present a user interface having one or more markings conveying that the verification bypass is inactive. In some embodiments, other markings included in that user interface can convey action(s) to be taken by an agent as a result of the verification bypass being inactive. In some embodiments, the verification bypass subsystem 130 can include a verification module 240 (FIG. 2) that can determine if the time interval exceeds the defined duration. The verification module 240 also can perform one or more exception operations. As is shown in FIG. 2, configuration module 210 can be functionally coupled to the memory 250 to output data to and retrieve data from the memory 250. The bus architecture (represented by arrows in FIG. 2) can permit the functional coupling between the configuration module 210 and the memory 250.

In other cases, the verification bypass subsystem 130 can determine that the time interval does not exceed the defined duration—e.g., the time interval is less than or equal to the defined duration. In response, the verification bypass subsystem 130 can designate the unit-of-use package as a verified item. Accordingly, the verification bypass subsystem 130 verifies the unit-of-use package automatically, without human intervention. In addition, as mentioned, the agent account that has permission to activate verification bypass for the first automation device can include data identifying a pharmacist. Hence, in further response to determining that the time interval does not exceed the defined duration, the verification bypass subsystem 130 can generate a data record identifying the pharmacist as a pharmacist of record for the unit-of-use package that has been dispensed from the first automation device. Additionally, the verification bypass subsystem 130 can retain the data record within data storage 160. The data storage 160 can retain various types of data corresponding to fulfillment of prescriptions at the dispensing pharmacy that includes the operating environment 100. In some embodiments, the verification module 240 (FIG. 2) can designate unit-of-use packages as a verified items. The verification module 240 also can retain data records of dispense of unit-of-use packages, where such data records can include data identifying the pharmacist as a pharmacist of record.

The active verification bypass can be terminated asynchronously during dispense of unit-of-use packages by one or more of the group of automation devices 114. Accordingly, in some scenarios, the verification bypass subsystem 130 can receive input data indicative of termination of the active verification bypass for a particular automation device having an active verification bypass. The particular automation device can dispense units-of-use packages as part of an automation process to fulfill prescription fill requests. The verification bypass subsystem 130 can then cause the state of the verification bypass for the particular automation device to transition to an in inactive state, resulting in the deactivation of the verification bypass.

Figure 4:
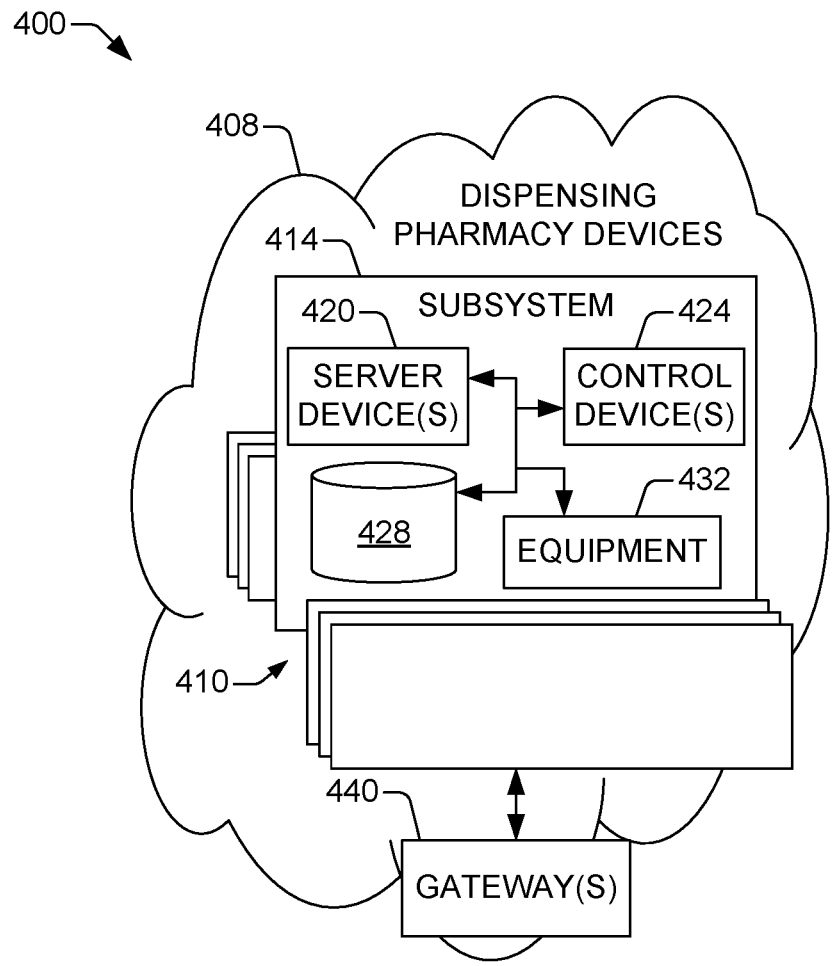
FIG. 4 illustrates an example of an architecture of an automated dispensing pharmacy, in accordance with one or more embodiments of this disclosure.

FIG. 4 is a schematic block diagram of an architecture 400 of the automated dispensing pharmacy that includes the operating environment 100, in accordance with one or more embodiments of this disclosure. As is described herein, the automated dispensing pharmacy can implement automation processes to fulfill prescription fill requests involving dispense of unit-of-use packages. To that end, as is illustrated in FIG. 4, the automated dispensing pharmacy includes dispensing pharmacy devices 408 that can include multiple subsystems 410 and one or multiple gateways 440. At least one of the subsystems 410 can embody, or can include, the verification bypass subsystem 130. Data storage included in one or more of the subsystems 410 can embody the data storage 160, in some embodiments. At least one of the gateway(s) 440 can be functionally coupled to one or more of the multiple subsystems 410. A gateway of the gateway(s) 440 can receive prescription fill requests and can route the prescription fill requests to an intake subsystem included in the multiple subsystems 410. Several of the subsystems 410 can include components that can implement an automation process to fulfill a prescription request.

The subsystem 414 shown in FIG. 4 illustrates an example of such subsystems. The subsystem 414 includes one or multiple server devices 420 that can administer the automation process. The subsystem 414 also includes one or multiple memory devices 428 (which can be referred to as data storage 428). Although the data storage 428 is illustrated as being external to the server device(s) 420, there are configurations where at least a portion of the data storage 428 is integrated into at least one of the server device(s) 420. In some embodiments, the data storage 428 can embody, or can be part of, the data storage 132. In other embodiments, the data storage 428 can embody, or can include the data storage 160. The subsystem 414 further includes one or multiple control devices 424 and equipment 432. The equipment 432 can include hoppers, conveyance systems, camera devices, weight scales, RFID reader devices, printing devices, and similar equipment. The equipment 432 can include, for example, the equipment 110 (FIG. 1). The control device(s) 424 can control the operation of at least some of the equipment 432 in order to execute the automation process. A bus architecture (represented by connected arrows) permit exchanging data and/or signaling among the server device(s) 420, the control device(s) 424, the equipment 432, and the data storage 428.

Because the architecture 400 can by the verification stage of each prescription involving a unit-of-use package, the efficiency of automation processes to fulfill prescriptions involving unit-of-use packages can be improved relative to existing prescription fulfillment process flows. Further, the footprint of such an architecture can be reduced relative to existing automated dispensing pharmacies. As a result, use space and consumption of energy can be improved.

Figure 5:
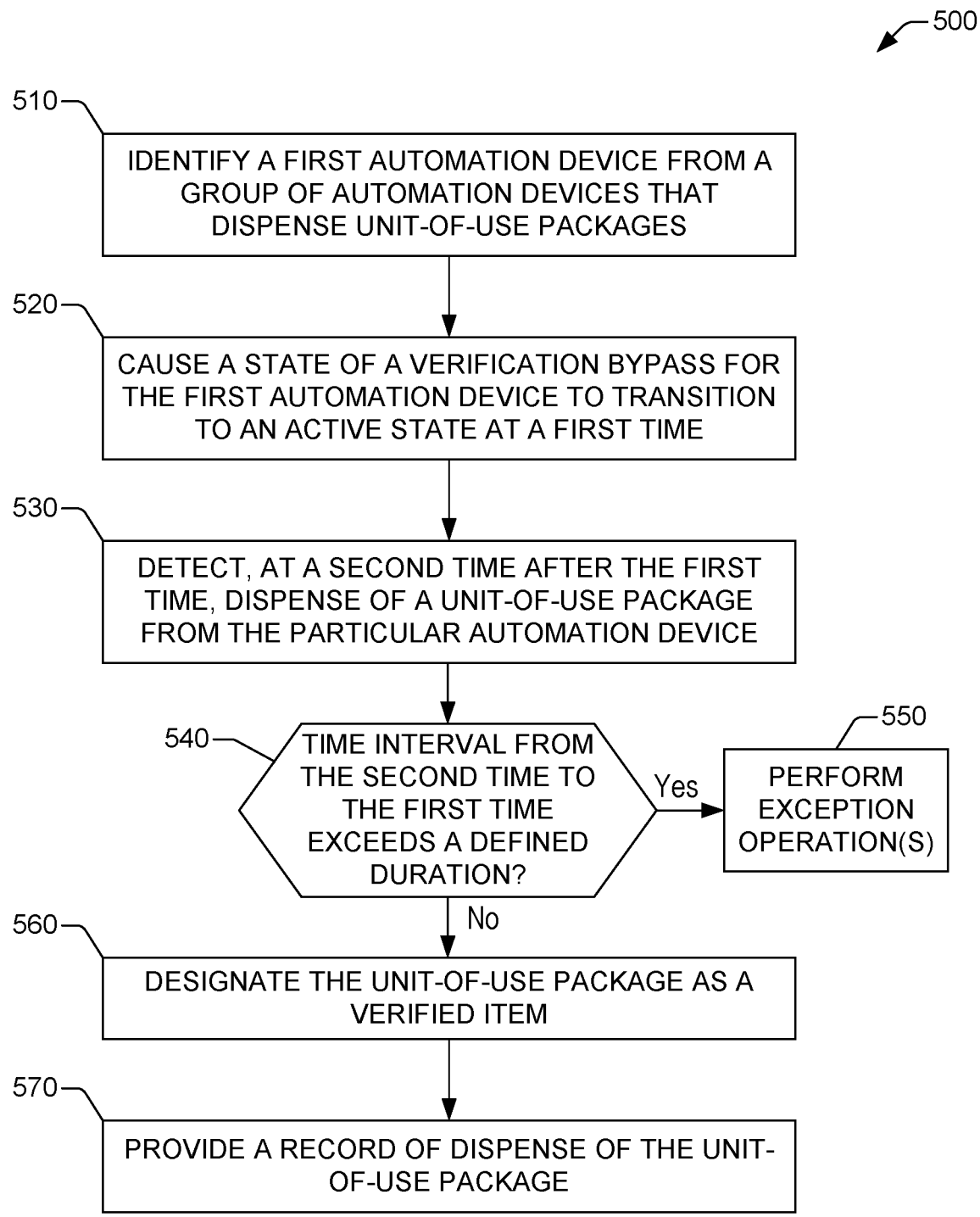
FIG. 5 illustrates an example of a method for implementing verification bypass in a dispensing pharmacy, in accordance with one or more embodiments of this disclosure.

FIG. 5 illustrates an example of a method 500 for implementing verification bypass in a dispensing pharmacy, in accordance with one or more embodiments of this disclosure. A computing system can perform the example method 500 in its entirety or in part. To that end, the computing system includes computing resources that can implement at least one of the blocks included in the example method 500. The computing resources include, for example, central processing units (CPUs), graphics processing units (GPUs), tensor processing units (TPUs), memory, disk space, incoming bandwidth, and/or outgoing bandwidth, interface(s) (such as I/O interfaces or APIs, or both); controller devices(s); power supplies; a combination of the foregoing; and/or similar resources. For instance, the computing system can include programming interface(s); an operating system; software for configuration and or control of a virtualized environment; firmware; and similar resources. In some embodiments, the computing system can embody, or can include, one or a combination of the verification bypass subsystem 130 (FIG. 1). The computing system can be integrated into a dispensing pharmacy and, thus, can be referred to as a dispensing pharmacy system.

At block 510, the dispensing pharmacy system can identify a first automation device from a group of automation devices. Each automation device of the group of automation devices dispenses unit-of-use packages (e.g., blister packs, metered-dose inhalers, course-of-therapy vials, and similar). A first automation device can dispense unit-of-use packages for a first prescription medication, and a second automation device can dispense unit-of-use packages for a second prescription medication. The dispensing pharmacy system can identify the first automation device in several ways. In some embodiments, the dispensing pharmacy system can determine that an agent account has permission to activate verification bypass for items dispensed from the group of automation devices. The agent account can include data identifying a pharmacist, for example. Further, the dispensing pharmacy system can prompt selection of at least one automation device from the group of automation devices, and can receive input data indicative of a selection of the first automation device from the group of automation devices.

In some embodiments, determining that the agent account has permission to activate verification bypass can include accessing data indicative of a group of permissions corresponding to the agent account, and determining that the group of permissions include the permission to activate a verification bypass.

The dispensing pharmacy system can generate data defining the group of automation devices. Accordingly, although not depicted in FIG. 5, in some embodiments of the example method 500, the dispensing pharmacy system can determine that an automation device within the dispensing pharmacy is eligible for verification bypass. The dispensing pharmacy system can then add data identifying the automation device to a data structure identifying the group of automation devices.

At block 520, the dispensing pharmacy system can cause a state of verification bypass for the first automation device to transition to an active state at a first time. In some embodiments, causing that state to transition to an active state can include updating a value of a state attribute to a new value indicative of the verification bypass being active.

At block 530, the dispensing pharmacy system can detect dispense of an item from the particular automation device. Dispense of the unit-of-use package can be detected at a second time after the first time. Detecting dispense of the item can include monitoring signaling from a control device that controls operation of the first automation device, as is described hereinbefore.

At block 540, the dispensing pharmacy system can determine if a time interval elapsed from the first time to the second time exceeds a defined duration. In other words, the dispensing pharmacy system can determine if that time interval is less than or equal to the defined duration. The defined duration is the lifespan of the active state of the verification bypass. The defined duration can be configurable. To configure the defined duration, in some embodiments, the example method 500 can include (not depicted in FIG. 5) prompting configuration of the defined duration of the active state of the verification bypass, and receiving input data indicative of the defined duration. For example, a server device included in the dispensing pharmacy system can cause a display device to present, or continue presenting, a UI that includes a selectable UI element. Selection of the selectable UI element can permit receiving the input data indicative of the defined duration.

In response to determining, at block 540, that the time interval exceeds the defined duration, the dispensing pharmacy system can perform one or multiple exception operations at block 550. In the alternative, the flow of the example method can continue to block 560 in response to determining that the time interval does not exceed the defined duration—e.g., the time interval is less than or equal to the defined duration. At block 560, the dispensing pharmacy system can designate the unit-of-use package as a verified item.

Further, at block 570, the dispensing pharmacy system provide a record of dispense of the unit-of-use package. As mentioned, the agent account can include data identifying a pharmacist. Thus, in some embodiments, providing the record of dispense of the unit-of-use package can include generating a data record identifying the pharmacist as a pharmacist of record for the unit-of-use package that has been dispensed, and retaining the data record within a storage device within the dispensing pharmacy. The storage device can be a part of data storage (e.g., the data storage 160 (FIG. 1) that retains various types of data corresponding to fulfillment of prescriptions at the dispensing pharmacy.

The active verification bypass can be terminated asynchronously during dispense of unit-of-use packages by one or more of the group of automation devices. Accordingly, although not depicted in FIG. 5, in some embodiments of the example method 500, the dispensing pharmacy system can receive input data indicative of termination of the active verification bypass. The dispensing pharmacy system can then cause the state of the verification bypass to transition to an in inactive state, resulting in the deactivation of the verification bypass.

Figure 6:
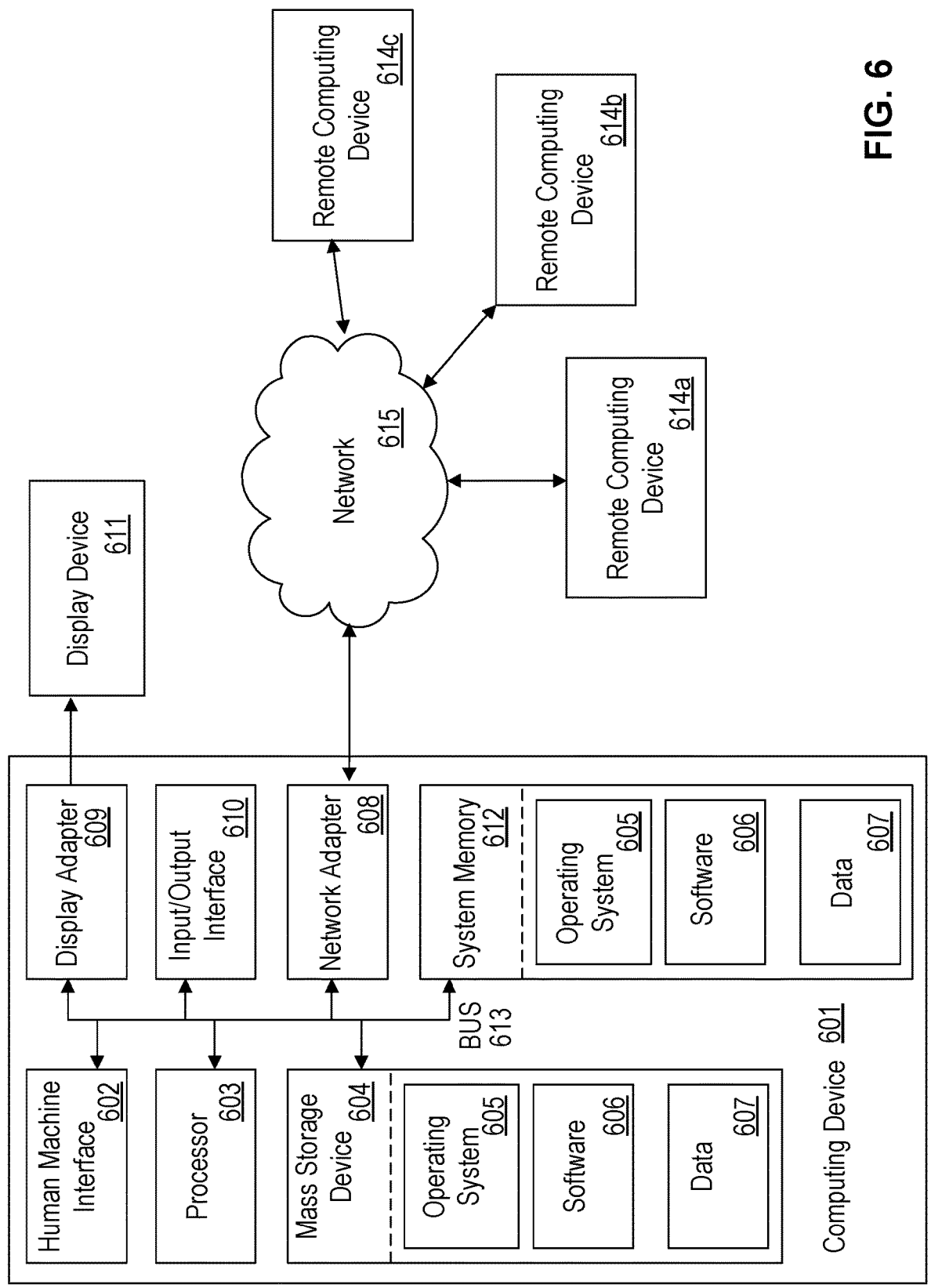
FIG. 6 illustrates an example of another operating environment that can implement verification bypass in a dispensing pharmacy, in accordance with one or more embodiments of this disclosure.

In order to provide some context, the computer-implemented methods and systems of this disclosure can be implemented on the computing environment illustrated in FIG. 6 and described below. Similarly, the computer-implemented methods and systems disclosed herein can utilize one or more computing devices to perform one or more functions in one or more locations. FIG. 6 is a block diagram illustrating an example of a computing environment for performing the disclosed methods and/or implementing the disclosed systems. The operating environment shown in FIG. 6 is only an example of an operating environment and is not intended to suggest any limitation as to the scope of use or functionality of operating environment architecture. Neither should the operating environment be interpreted as having any dependency or requirement relating to any one or combination of components illustrated in the exemplary operating environment. The operating environment shown in FIG. 6 can embody at least a portion of the operating environment 100 (FIG. 1) or the architecture shown in FIG. 2.

The computer-implemented methods and systems in accordance with this disclosure can be operational with numerous other general purpose or special purpose computing system environments or configurations. Examples of well-known computing systems, environments, and/or configurations that can be suitable for use with the systems and methods comprise, but are not limited to, personal computers, server computers, laptop devices, and multiprocessor systems. Additional examples comprise set-top boxes, programmable consumer electronics, network PCs, minicomputers, mainframe computers, distributed computing environments that comprise any of the above systems or devices, and the like.

The processing of the disclosed computer-implemented methods and systems can be performed by software components. The disclosed systems and computer-implemented methods can be described in the general context of computer-executable instructions, such as program modules, being executed by one or more computers or other devices. Generally, program modules comprise computer code, routines, programs, objects, components, data structures, etc. that perform particular tasks or implement particular abstract data types. The disclosed methods can also be practiced in grid-based and distributed computing environments where tasks are performed by remote processing devices that are linked through a communications network. In a distributed computing environment, program modules can be located in both local and remote computer storage media including memory storage devices.

Further, one skilled in the art will appreciate that the systems and computer-implemented methods disclosed herein can be implemented via a general-purpose computing device in the form of a computing device 601. The components of the computing device 601 can comprise, but are not limited to, one or more processors 603, a system memory 612, and a system bus 613 that couples various system components including the one or more processors 603 to the system memory 612. The system can utilize parallel computing.

The system bus 613 represents one or more of several possible types of bus structures, including a memory bus or memory controller, a peripheral bus, an accelerated graphics port, or local bus using any of a variety of bus architectures. The bus 613, and all buses specified in this description can also be implemented over a wired or wireless network connection and each of the subsystems, including the one or more processors 603, a mass storage device 604, an operating system 605, software 606, data 607, a network adapter 608, the system memory 612, an Input/Output Interface 610, a display adapter 609, a display device 611, and a human-machine interface 602, can be contained within one or more remote computing devices 614a,b,c at physically separate locations, connected through buses of this form, in effect implementing a fully distributed system.

The computing device 601 typically comprises a variety of computer-readable media. Exemplary readable media can be any available media that is accessible by the computing device 601 and comprises, for example and not meant to be limiting, both volatile and non-volatile media, removable and non-removable media. The system memory 612 comprises computer readable media in the form of volatile memory, such as random access memory (RAM), and/or non-volatile memory, such as read only memory (ROM). The system memory 612 typically contains data such as the data 607 and/or program modules such as the operating system 605 and the software 606 that are immediately accessible to and/or are presently operated on by the one or more processors 603. The software 606 can include, in some embodiments, one or more of the modules described herein in connection with verification bypass in a dispensing pharmacy. As such, in at least some of those embodiments, the software 606 can include the configuration module 210, the access module 220, the detection module 230, and the verification module 240. In other embodiments, the software 606 can include a different configuration of modules from that shown in FIG. 2, while still providing the functionality described herein in connection with the configuration module 210, the access module 220, the detection module 230, and the verification module 240. The data 607 can include data retained in data storage 132 (FIG. 1).

In some embodiments, program modules that constitute the software 606 can be retained (built or otherwise) in one or more remote computing devices functionally coupled to the computing device 601. Such remote computing device(s) can include, for example, remote computing device 614a, remote computing device 614b, and remote computing device 614c. Hence, as mentioned, functionality described herein in connection with detection of anomalous record can be provided in a distributed fashion, using parallel computing, for example. Data storage present in one or more of the remote computing device(s) can include the data storage 160 (FIG. 1), in some embodiments.

In another aspect, the computing device 601 can also comprise other removable/non-removable, volatile/non-volatile computer storage media. By way of example, FIG. 6 illustrates the mass storage device 604 which can provide non-volatile storage of computer code, computer readable instructions, data structures, program modules, and other data for the computing device 601. For example and not meant to be limiting, the mass storage device 604 can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Optionally, any number of program modules can be stored on the mass storage device 604, including by way of example, the operating system 605 and the software 606. Each of the operating system 605 and the software 606 (or some combination thereof) can comprise elements of the programming and the software 606. The data 607 can also be stored on the mass storage device 604. The data 607 can be stored in any of one or more databases known in the art. Examples of such databases comprise, DB2®, Microsoft® Access, Microsoft® SQL Server, Oracle®, mySQL, PostgreSQL, and the like. The databases can be centralized or distributed across multiple systems.

In another aspect, the user can enter commands and information into the computing device 601 via an input device (not shown). Examples of such input devices comprise, but are not limited to, a keyboard, pointing device (e.g., a "mouse"), a microphone, a joystick, a scanner, tactile input devices such as gloves, and other body coverings, and the like These and other input devices can be connected to the one or more processors 603 via the human-machine interface 602 that is coupled to the system bus 613, but can be connected by other interface and bus structures, such as a parallel port, game port, an IEEE 1394 Port (also known as a Firewire port), a serial port, or a universal serial bus (USB).

In yet another aspect, the display device 611 can also be connected to the system bus 613 via an interface, such as the display adapter 609. It is contemplated that the computing device 601 can have more than one display adapter 609 and the computing device 601 can have more than one display device 611. For example, the display device 611 can be a monitor, an LCD (Liquid Crystal Display), or a projector. In addition to the display device 611, other output peripheral devices can comprise components such as speakers (not shown) and a printer (not shown) which can be connected to the computing device 601 via the Input/Output Interface 610. Any operation and/or result of the methods can be output in any form to an output device. Such output can be any form of visual representation, including, but not limited to, textual, graphical, animation, audio, tactile, and the like. The display device 611 and computing device 601 can be part of one device, or separate devices.

The computing device 601 can operate in a networked environment using logical connections to one or more remote computing devices 614*a,b,c*. By way of example, a remote computing device can be a personal computer, portable computer, smartphone, a server, a router, a network computer, a peer device or other common network node, and so on. Logical connections between the computing device 601 and a remote computing device 614*a,b,c* can be made via a network 615, such as a local area network (LAN) and/or a general wide area network (WAN). Such network connections can be through the network adapter 608. The network adapter 608 can be implemented in both wired and wireless environments. In an aspect, one or more of the remote computing devices 614*a,b,c* can comprise an external engine and/or an interface to the external engine.

For purposes of illustration, application programs and other executable program components such as the operating system 605 are illustrated herein as discrete blocks, although it is recognized that such programs and components reside at various times in different storage components of the computing device 601, and are executed by the one or more processors 603 of the computer. An implementation of the software 606 can be stored on or transmitted across some form of computer-readable media. Any of the disclosed methods can be performed by computer readable instructions embodied on computer-readable media. Computer-readable media can be any available media that can be accessed by a computer. By way of example and not meant to be limiting, computer-readable media can comprise "computer storage media" and "communications media." "Computer storage media" comprise volatile and non-volatile, removable and non-removable media implemented in any methods or technology for storage of information such as computer-readable instructions, data structures, program modules, or other data. Exemplary computer storage media comprises, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

It is to be understood that the methods and systems described here are not limited to specific operations, processes, components, or structure described, or to the order or particular combination of such operations or components as described. It is also to be understood that the terminology used herein is for the purpose of describing exemplary embodiments only and is not intended to be restrictive or limiting.

As used herein the singular forms "a," "an," and "the" include both singular and plural referents unless the context clearly dictates otherwise. Values expressed as approximations, by use of antecedents such as "about" or "approximately," shall include reasonable variations from the referenced values. If such approximate values are included with ranges, not only are the endpoints considered approximations, the magnitude of the range shall also be considered an approximation. Lists are to be considered exemplary and not restricted or limited to the elements comprising the list or to the order in which the elements have been listed unless the context clearly dictates otherwise.

Throughout the specification and claims of this disclosure, the following words have the meaning that is set forth: "comprise" and variations of the word, such as "comprising" and "comprises," mean including but not limited to, and are not intended to exclude, for example, other additives, components, integers, or operations. "Include" and variations of the word, such as "including" are not intended to mean something that is restricted or limited to what is indicated as being included, or to exclude what is not indicated. "May" means something that is permissive but not restrictive or limiting. "Optional" or "optionally" means something that may or may not be included without changing the result or what is being described. "Prefer" and variations of the word such as "preferred" or "preferably" mean something that is exemplary and more ideal, but not required. "Such as" means something that serves simply as an example.

Operations and components described herein as being used to perform the disclosed methods and construct the disclosed systems are illustrative unless the context clearly dictates otherwise. It is to be understood that when combinations, subsets, interactions, groups, etc. of these operations and components are disclosed, that while specific reference of each various individual and collective combinations and permutation of these may not be explicitly disclosed, each is specifically contemplated and described herein, for all methods and systems. This applies to all aspects of this application including, but not limited to, operations in disclosed methods and/or the components disclosed in the systems. Thus, if there are a variety of additional operations that can be performed or components that can be added, it is understood that each of these additional operations can be performed and components added with any specific embodiment or combination of embodiments of the disclosed systems and methods.

Embodiments of this disclosure may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. Any suitable computer-readable storage medium may be utilized including hard disks, CD-ROMs, optical storage devices, or magnetic storage devices, whether internal, networked, or cloud-based.

Embodiments of this disclosure have been described with reference to diagrams, flowcharts, and other illustrations of computer-implemented methods, systems, apparatuses, and computer program products. Each block of the block diagrams and flowchart illustrations, and combinations of blocks in the block diagrams and flowchart illustrations, respectively, can be implemented by processor-accessible instructions. Such instructions can include, for example, computer program instructions (e.g., processor-readable and/or processor-executable instructions). The processor-accessible instructions can be built (e.g., linked and compiled) and retained in processor-executable form in one or multiple memory devices or one or many other processor-accessible non-transitory storage media. These computer program instructions (built or otherwise) may be loaded onto a general-purpose computer, special purpose computer, or other programmable data processing apparatus to produce a machine. The loaded computer program instructions can be accessed and executed by one or multiple processors or other types of processing circuitry. In response to execution, the loaded computer program instructions provide the functionality described in connection with flowchart blocks (individually or in a particular combination) or blocks (individually or in a particular combination) in block diagrams. Thus, such instructions which execute on the computer or other programmable data processing apparatus create a means for implementing the functions specified in the flowchart blocks (individually or in a particular combination) or blocks (individually or in a particular combination) in block diagrams.

These computer program instructions may also be stored in a computer-readable memory that can direct a computer or other programmable data processing apparatus to function in a particular manner, such that the instructions stored in the computer-readable memory produce an article of manufacture including processor-accessible instruction (e.g., processor-readable instructions and/or processor-executable instructions) to implement the function specified in the flowchart blocks (individually or in a particular combination) or blocks (individually or in a particular combination) in block diagrams. The computer program instructions (built or otherwise) may also be loaded onto a computer or other programmable data processing apparatus to cause a series of operations to be performed on the computer or other programmable apparatus to produce a computer-implemented process. The series of operations can be performed in response to execution by one or more processor or other types of processing circuitry. Thus, such instructions that execute on the computer or other programmable apparatus provide operations that implement the functions specified in the flowchart blocks (individually or in a particular combination) or blocks (individually or in a particular combination) in block diagrams.

Accordingly, blocks of the block diagrams and flowchart illustrations support combinations of means for performing the specified functions in connection with such diagrams and/or flowchart illustrations, combinations of operations for performing the specified functions and program instruction means for performing the specified functions. Each block of the block diagrams and flowchart illustrations, and combinations of blocks in the block diagrams and flowchart illustrations, can be implemented by special purpose hardware-based computer systems that perform the specified functions or operations, or combinations of special purpose hardware and computer instructions.

The computer-implemented methods and systems can employ artificial Intelligence techniques such as machine learning and iterative learning. Examples of such techniques include, but are not limited to, expert systems, case-based reasoning, Bayesian networks, behavior-based AI, neural networks, fuzzy systems, evolutionary computation (e.g. genetic algorithms), swarm intelligence (e.g. ant algorithms), and hybrid intelligent systems (e.g. expert inference rules generated through a neural network or production rules from statistical learning).

While the computer-implemented methods, apparatuses, devices, and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its operations be performed in a specific order. Accordingly, where a method claim does not actually recite an order to be followed by its operations or it is not otherwise specifically stated in the claims or descriptions that the operations are to be limited to a specific order, it is in no way intended that an order be inferred, in any respect. This holds for any possible non-express basis for interpretation, including: matters of logic with respect to arrangement of operations or operational flow; plain meaning derived from grammatical organization or punctuation; the number or type of embodiments described in the specification.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A computing system, comprising:
   at least one processor; and
   at least one memory device having processor-executable instructions stored thereon that,
   in response to execution by the at least one processor, cause the computing system to:
   identify a first automation device from a group of automation devices that dispense unit-of-use packages;

cause a state of a verification bypass for the first automation device to transition to an active state at a first time;

detect, at a second time after the first time, dispense of a unit-of-use package from the first automation device;

determine that a time interval elapsed from the first time to the second time is less than or equal to a defined duration; and designate the unit-of-use package as a verified item in response to detecting the dispense of the unit-of-use package.

2. The computing system of claim 1, the at least one memory device having further processor-executable instructions stored thereon that in response to execution by the at least one processor further cause the computing system to, prompt configuration of the defined duration of the active state of the verification bypass; and receive input data indicative of the defined duration.

3. The computing system of claim 1, the at least one memory device having further processor-executable instructions stored thereon that in response to execution by the at least one processor further cause the computing system to, receive input data indicative of deactivation of the verification bypass; and cause the state of the verification bypass to transition to an inactive state.

4. The computing system of claim 1, wherein identifying the first automation device from the group of automation devices comprises, determining that an agent account has permission to activate the verification bypass for the unit-of-use packages dispensed from the group of automation devices;

prompting selection of at least one automation device from the group of automation devices; and receiving input data indicative of a selection of the first automation device from the group of automation devices.

5. The computing system of claim 4, wherein determining that the agent account has permission to activate the verification bypass comprises, accessing data indicative of a group of permissions corresponding to the agent account; and determining that the group of permissions comprises the permission to activate the verification bypass.

6. The computing system of claim 5, wherein the agent account comprises data identifying a pharmacist, the at least one memory device having further processor-executable instructions stored thereon that in response to execution by the at least one processor further cause the computing system to, generate a data record identifying the pharmacist as a pharmacist of record for the unit-of-use package; and retain the data record within a storage device at a dispensing pharmacy.

7. The computing system of claim 1, the at least one memory device having further processor-executable instructions stored thereon that in response to execution by the at least one processor further cause the computing system to, determine that a particular automation device is eligible for the verification bypass; and add data identifying the particular automation device to a data structure identifying the group of automation devices.

8. A method, comprising:

identifying, by a dispensing pharmacy system, a first automation device from a group of automation devices that dispense unit-of-use packages;

causing, by the dispensing pharmacy system, a state of a verification bypass for the first automation device to transition to an active state at a first time;

detecting, by the dispensing pharmacy system, at a second time after the first time, dispense of a unit-of-use package from the first automation device;

determining, by the dispensing pharmacy system, that a time interval elapsed from the first time to the second time is less than or equal to a defined duration; and designating, by the dispensing pharmacy system, the unit-of-use package as a verified item in response to detecting the dispense of the unit-of-use package.

9. The method of claim 8, further comprising, prompting, by the dispensing pharmacy system, configuration of the defined duration of the active state of the verification bypass; and receiving, by the dispensing pharmacy system, input data indicative of the defined duration.

10. The method of claim 8, further comprising, receiving, by the dispensing pharmacy system, input data indicative of deactivation of the verification bypass; and causing, by the dispensing pharmacy system, the state of the verification bypass to transition to an inactive state.

11. The method of claim 8, wherein the identifying comprises, determining that an agent account has permission to activate the verification bypass for the unit-of-use packages dispensed from the group of automation devices;

prompting selection of at least one automation device from the group of automation devices; and receiving input data indicative of a selection of the first automation device from the group of automation devices.

12. The method of claim 11, wherein the determining comprises, accessing data indicative of a group of permissions corresponding to the agent account; and determining that the group of permissions comprises the permission to activate the verification bypass.

13. The method of claim 12, wherein the agent account comprises data identifying a pharmacist, the method further comprising, generating, by the dispensing pharmacy system, a data record identifying the pharmacist as a pharmacist of record for the unit-of-use package; and storing, by the dispensing pharmacy system, the data record within a storage device at a dispensing pharmacy.

14. The method of claim 8, further comprising, determining, by the dispensing pharmacy system, that a particular automation device is eligible for the verification bypass; and adding, by the dispensing pharmacy system, data identifying the particular automation device to a data structure identifying the group of automation devices.

15. At least one computer-readable non-transitory storage medium having processor-executable instructions stored thereon that, in response to execution, cause a computing system to:

identify a first automation device from a group of automation devices that dispense unit-of-use packages;

cause a state of a verification bypass for the first automation device to transition to an active state at a first time;

detect, at a second time after the first time, dispense of a unit-of-use package from the first automation device;

determine that a time interval elapsed from the first time to the second time is less than or equal to a defined duration; and designate the unit-of-use package as a verified item in response to detecting the dispense of the unit-of-use package.

16. The at least one computer-readable non-transitory storage medium of claim 15, wherein the processor-executable instructions further cause the computing system to, prompt configuration of the defined duration of the active state of the verification bypass; and receive input data indicative of the defined duration.

17. The at least one computer-readable non-transitory storage medium of claim 15, wherein the processor-executable instructions further cause the computing system to, receive input data indicative of deactivation of the verification bypass; and cause the state of the verification bypass to transition to an inactive state.

18. The at least one computer-readable non-transitory storage medium of claim 15, wherein identifying the first automation device from the group of automation devices comprises, determining that an agent account has permission to activate the verification bypass for the unit-of-use packages dispensed from the group of automation devices;

prompting selection of at least one automation device from the group of automation devices; and receiving input data indicative of a selection of the first automation device from the group of automation devices.

19. The at least one computer-readable non-transitory storage medium of claim 18, wherein the agent account comprises data identifying a pharmacist, and wherein the processor-executable instructions, in response to further execution, further cause the computing system to, generate a data record identifying the pharmacist as a pharmacist of record for the unit-of-use package; and retain the data record within a storage device at a dispensing pharmacy.

20. The at least one computer-readable non-transitory storage medium of claim 15, wherein the processor-executable instructions, in response to further execution, further cause the computing system to, determine that a particular automation device is eligible for the verification bypass; and add data identifying the particular automation device to a data structure identifying the group of automation devices.

* * * * *